US007682021B2

(12) United States Patent
Sabel (10) Patent No.: US 7,682,021 B2
(45) Date of Patent: Mar. 23, 2010

(54) SYSTEM AND METHODS FOR THE TREATMENT OF RETINAL DISEASES

(75) Inventor: Bernhard Sabel, Berlin (DE)

(73) Assignee: NovaVision, Inc., Boca Raton, FL (US)

( * ) Notice: Subject to any disclaimer, the term of this patent is extended or adjusted under 35 U.S.C. 154(b) by 0 days.

(21) Appl. No.: 11/343,960

(22) Filed: Jan. 31, 2006

(65) Prior Publication Data

US 2006/0283466 A1    Dec. 21, 2006

Related U.S. Application Data

(63) Continuation-in-part of application No. 10/503,869, filed as application No. PCT/EP02/01339 on Feb. 8, 2002, now Pat. No. 7,367,671.

(51) Int. Cl.
*A61B 3/00* (2006.01)
*A61B 3/02* (2006.01)
*A61H 33/00* (2006.01)

(52) U.S. Cl. ............................ 351/203; 351/222; 607/87
(58) Field of Classification Search ................ 351/200, 351/201, 203, 222–224, 246, 46; 607/87–88; 606/2
See application file for complete search history.

(56) References Cited

U.S. PATENT DOCUMENTS

| 1,463,847 | A | 8/1923 | Shilling | |
| 2,213,484 | A | 9/1940 | Briggs | 128/76.5 |
| 3,883,234 | A | 5/1975 | Lynn et al. | 351/23 |
| 4,260,227 | A | 4/1981 | Munnerlyn et al. | 351/24 |
| 4,408,846 | A | 10/1983 | Balliet | 351/203 |
| 4,421,392 | A | 12/1983 | Pitts Crick et al. | 351/224 |
| 4,429,961 | A | 2/1984 | Sheingorn | 351/226 |
| 4,533,221 | A | 8/1985 | Trachtman | 351/203 |
| 4,660,945 | A | 4/1987 | Trachtman | 351/203 |
| 4,679,920 | A | 7/1987 | Takashi et al. | 351/226 |
| 4,971,434 | A | 11/1990 | Ball | 351/224 |

(Continued)

FOREIGN PATENT DOCUMENTS

DE    9305147    4/1994

(Continued)

OTHER PUBLICATIONS

Portable Tech/Emory Device Checks for Concussions, http://www.gatech.edu/news-room/release.php?id=554, Apr. 26, 2005.

(Continued)

*Primary Examiner*—Ricky L Mack
*Assistant Examiner*—Dawayne A Pinkney
(74) *Attorney, Agent, or Firm*—Sunstein Kann Murphy & Timbers LLP (57) ABSTRACT

Systems and methods for treating a retinal disease in a human include locating and defining one or more zones of vision within the human's visual system and defining a treatment area which is located within at least one of the zones. The method of this embodiment may also include treating the human's retinal disease by presenting visual stimuli to the treatment area at a specified location and with a specified definition and recording changes in specified characteristics of the human's visual system. The method of this embodiment may also include reiterating the previous steps so as to improve the human's overall visual system.

52 Claims, 5 Drawing Sheets

VS = Visual Field
MF = Monitor Frame
B = Blind Region
TZ = Transition Zone
TS1 = Target Stimulus 1
TS2 = Target Stimulus 2
F = Fixation Point
I = Intact Visual Field Sector

U.S. PATENT DOCUMENTS

| | | | |
|---|---|---|---|
| 4,995,717 A | 2/1991 | Damato | 351/224 |
| 5,035,500 A | 7/1991 | Rorabaugh et al. | 351/226 |
| 5,050,982 A | 9/1991 | Meissner | 351/203 |
| 5,088,810 A | 2/1992 | Galanter et al. | 351/203 |
| 5,139,323 A * | 8/1992 | Schillo | 351/45 |
| 5,147,284 A | 9/1992 | Fedorov et al. | 600/9 |
| 5,191,367 A | 3/1993 | Salibello et al. | 351/243 |
| 5,206,671 A | 4/1993 | Eydelman et al. | 351/203 |
| 5,241,332 A | 8/1993 | Farrell | 351/246 |
| 5,305,027 A | 4/1994 | Patterson | 351/44 |
| 5,321,445 A | 6/1994 | Fossetti | 351/203 |
| 5,325,136 A | 6/1994 | Salibello et al. | 351/243 |
| 5,363,154 A | 11/1994 | Galanter et al. | 351/203 |
| 5,455,643 A | 10/1995 | Ki-Ho | 351/203 |
| 5,534,953 A | 7/1996 | Schmielau | 351/203 |
| 5,539,481 A | 7/1996 | Vax | 351/203 |
| 5,539,482 A | 7/1996 | James et al. | 351/246 |
| 5,550,602 A | 8/1996 | Braeuning | 351/243 |
| 5,565,949 A | 10/1996 | Kasha, Jr. | 351/224 |
| 5,883,692 A | 3/1999 | Agonis et al. | 351/203 |
| 5,886,770 A * | 3/1999 | Damato | 351/237 |
| 5,912,723 A | 6/1999 | Maddess | 351/246 |
| 5,946,075 A | 8/1999 | Horn | 351/246 |
| 5,991,085 A | 11/1999 | Rallison et al. | 359/630 |
| 6,062,687 A | 5/2000 | Lofgren-Nisser | 351/46 |
| 6,286,960 B1 | 9/2001 | Tomita | 351/245 |
| 6,321,338 B1 | 11/2001 | Porras et al. | 713/201 |
| 6,359,601 B1 | 3/2002 | Maguire, Jr. | 345/7 |
| 6,364,486 B1 | 4/2002 | Ball et al. | 351/203 |
| 6,386,706 B1 | 5/2002 | McClure et al. | 351/237 |
| 6,406,437 B1 | 6/2002 | Zur et al. | 600/558 |
| 6,431,708 B2 | 8/2002 | Krebs | 351/203 |
| 6,443,977 B1 | 9/2002 | Jaillet | 607/88 |
| 6,464,356 B1 * | 10/2002 | Sabel et al. | 351/203 |
| 6,519,703 B1 | 2/2003 | Joyce | 713/201 |
| 6,540,355 B1 | 4/2003 | Couture | 351/203 |
| 6,578,966 B2 | 6/2003 | Fink et al. | 351/237 |
| 6,592,221 B1 | 7/2003 | Stregova | 351/203 |
| 6,656,131 B2 | 12/2003 | Alster et al. | 600/558 |
| 6,688,746 B2 | 2/2004 | Malov | 351/239 |
| 6,742,892 B2 | 6/2004 | Liberman | 351/203 |
| 6,769,770 B2 | 8/2004 | Fink et al. | 351/239 |
| 6,990,377 B2 | 1/2006 | Gliner et al. | 607/54 |
| 7,004,912 B2 | 2/2006 | Polat | 600/558 |
| 7,104,659 B2 | 9/2006 | Grier et al. | 359/614 |
| 7,220,000 B2 | 5/2007 | Alster et al. | 351/224 |
| 7,275,830 B2 | 10/2007 | Alster et al. | 351/223 |
| 7,309,128 B2 | 12/2007 | Cappo et al. | 351/224 |
| 7,367,671 B2 | 5/2008 | Sabel | 351/203 |
| 2002/0024634 A1 | 2/2002 | Fink et al. | 351/237 |
| 2002/0047987 A1 | 4/2002 | Massengill et al. | 351/204 |
| 2002/0107960 A1 | 8/2002 | Wetherall et al. | 709/225 |
| 2002/0186179 A1 | 12/2002 | Knowles | 345/8 |
| 2003/0020873 A1* | 1/2003 | Fink et al. | 351/200 |
| 2003/0090439 A1 | 5/2003 | Spitzer et al. | 345/8 |
| 2003/0156254 A1 | 8/2003 | Turovetsky | 351/203 |
| 2003/0214630 A1 | 11/2003 | Winterbotham | 351/203 |
| 2004/0012758 A1 | 1/2004 | Lin | 351/203 |
| 2004/0051848 A1 | 3/2004 | Gotze et al. | 351/203 |
| 2004/0075811 A1 | 4/2004 | Liberman | 351/203 |
| 2004/0100616 A1 | 5/2004 | Eremeev | 351/203 |
| 2004/0257528 A1 | 12/2004 | Miyake et al. | 351/203 |
| 2005/0001980 A1 | 1/2005 | Spector | 351/203 |
| 2005/0004624 A1 | 1/2005 | Gliner et al. | 607/54 |
| 2005/0041208 A1 | 2/2005 | Winterbotham | 351/203 |
| 2005/0122477 A1 | 6/2005 | Alster et al. | 351/237 |
| 2005/0213033 A1 | 9/2005 | Sabel | 351/203 |
| 2005/0213034 A1 | 9/2005 | Nagayoshi | 351/203 |
| 2005/0213035 A1 | 9/2005 | Yoshimeki et al. | 351/203 |
| 2006/0092377 A1 | 5/2006 | Todd et al. | 128/898 |
| 2006/0283466 A1 | 12/2006 | Sabel | 128/898 |
| 2006/0288258 A1 | 12/2006 | Lo et al. | 714/46 |
| 2006/0290885 A1 | 12/2006 | Covannon et al. | 351/212 |
| 2007/0038142 A1 | 2/2007 | Todd et al. | 600/558 |
| 2007/0121070 A1 | 5/2007 | Alster et al. | 351/224 |
| 2007/0171372 A1 | 7/2007 | Seal et al. | 351/245 |
| 2007/0182928 A1 | 8/2007 | Sabel | 351/224 |
| 2007/0216865 A1 | 9/2007 | Sabel et al. | 351/203 |
| 2008/0013047 A1 | 1/2008 | Todd et al. | 351/203 |
| 2008/0024724 A1 | 1/2008 | Todd | 351/222 |
| 2008/0043201 A1 | 2/2008 | Todd | 351/222 |
| 2008/0077437 A1 | 3/2008 | Mehta et al. | 705/2 |

FOREIGN PATENT DOCUMENTS

| | | |
|---|---|---|
| DE | 10207839 | 9/2002 |
| EP | 115263 | 8/1984 |
| EP | 128783 | 12/1984 |
| EP | 135736 | 8/1985 |
| EP | 0242723 | 10/1987 |
| EP | 0537945 A1 | 4/1993 |
| EP | 544631 | 6/1993 |
| EP | 689822 | 1/1996 |
| EP | 775464 | 5/1997 |
| EP | 830839 | 3/1998 |
| EP | 1186271 | 3/2002 |
| EP | 1236432 | 9/2002 |
| EP | 1236433 | 9/2002 |
| EP | 1384462 | 1/2004 |
| EP | 1402869 | 3/2004 |
| EP | 1403680 A1 | 3/2004 |
| GB | 1465561 | 2/1977 |
| WO | WO 8000405 | 3/1980 |
| WO | WO 8810088 | 12/1988 |
| WO | WO 9100553 | 1/1991 |
| WO | WO 9110393 | 7/1991 |
| WO | WO 9200037 | 1/1992 |
| WO | WO 9517227 | 6/1995 |
| WO | WO 9700653 | 1/1997 |
| WO | WO 9811819 | 3/1998 |
| WO | WO 9849992 | 11/1998 |
| WO | WO 9952419 | 10/1999 |
| WO | WO 9959461 | 11/1999 |
| WO | WO 0012042 | 3/2000 |
| WO | WO 0036971 | 6/2000 |
| WO | WO 0113859 | 3/2001 |
| WO | WO 0145630 | 6/2001 |
| WO | WO 0147463 | 7/2001 |
| WO | WO 0180808 | 11/2001 |
| WO | WO 0239754 | 1/2002 |
| WO | WO 0209578 | 2/2002 |
| WO | WO 02/39754 A.1 | 5/2002 |
| WO | WO 02053072 | 7/2002 |
| WO | WO 03002070 | 1/2003 |
| WO | WO 03002190 | 1/2003 |
| WO | WO 03007944 | 1/2003 |
| WO | WO 03020195 | 3/2003 |
| WO | WO 03041630 | 5/2003 |
| WO | WO 03065964 | 8/2003 |
| WO | WO 03092482 | 11/2003 |
| WO | WO 03092570 | 11/2003 |
| WO | WO 03098529 | 11/2003 |
| WO | WO 2004066900 | 8/2004 |
| WO | WO 2005004985 | 1/2005 |
| WO | WO 2005037177 | 4/2005 |
| WO | WO 2005044096 | 5/2005 |
| WO | WO 2005063153 | 7/2005 |
| WO | WO 2005092270 | 10/2005 |
| WO | WO 2005110326 | 11/2005 |
| WO | WO 2005122872 | 12/2005 |
| WO | WO 2006006563 | 1/2006 |
| WO | WO 2006002070 | 5/2006 |

| | | |
|---|---|---|
| WO | WO 2007109724 | 9/2007 |
| WO | WO 2008/077440 A1 | 7/2008 |

OTHER PUBLICATIONS

Erich Kasten et al., Computer-based training for the treatment of partial blindness, Nature Medicine, vol. 4, No. 9, pp. 1083-1087, Sep. 1998.

Burkhard Pleger et al., Functional magnetic resonance imaging mirrors recovery of visual perception after repetitive tachistoscopic stimulation in patients with partial cortical blindness, Neuroscience Letters, vol. 335, pp. 192-194, 2003.

Walter Widdig et al., Repetitive visual stimulation: A neuropsychological approach to the treatment of cortical blindness, NeuroRehabilitation, vol. 18, pp. 227-237, 2003.

Robert Sekuler, Vision Loss in an Aging Society: A Multidisciplinary Perspective/Vision Rehabilitation: Assessment, Intervention and Outcomes/The Lighthouse Handbook on Vision; Aug. 1, 2001, Gerontologist 556, vol. 41, Issue 4; ISSN: 0016-9013, © 2001.

Erich Kasten, Dorothe A. Poggel, Bernhard A. Sabel, Computer Based Training Stimulus Detection Improves Color and Simple Pattern Recognition in the Defective Field of Hemianopic Subjects; Nov. 1, 2000, Journal of Cognitive Neuroscience 1001, ISSN: 0898-929X; vol. 12, Issue 6; © 2000.

Rewiring Your Gray Matter: The brain: You can trach an old brain new tricks. Neuroplasticity promises to give a whole new meaning to 'changing your mind'; Jan. 1, 2000, Newsweek 63; ISSN: 0028-9604; vol. 134, issue 26, © 2000.

Teaching the brain to restore sight; Popular Mechanics, Jan. 18, 1999, Associated Press Newswires, © 1999.

Philip A. Schwartzkroin, Synaptic Plasticity: Molecular, Cellular, and Functional Aspects (book reviews); May 20, 1994, Science 1179; vol. 264, No. 5162, ISSN: 0036-8075; © 1994.

J. Zihl, et al., Restitution of visual function in patients with cerebral blindness; Zihl and von Cramon, J Neurol Neurosurg Psychiatry (1979).

J. Zihl, et al., Restitution of visual field in patients with damage to the geniculostriate visual pathway; Zihl and von Cramon, Human Neurobiology (1982).

E. Kasten, S. Wuest, B. Sabel, Journal of Clinical and Experimental Neuropsychology 1998, vol. 20, No. 5, pp. 581-598 "Residual Vision in Transition Zones in Patients with Cerebral Blindness".

F. Schmielau, Restitution of visual function in cases of brain damaged patients: Efficacy of localization specific sensory and sensomotoric rehabilitation procedures. In "Psychologie in der Neurologie" [Psychology in Neurology], P. Jacobi (editor). Berlin: Springer, 115-126(1989).

E. Kasten et al., Restoration of vision II: Residual functions and training-induced visual field enlargement in brain-damaged patients.

K.K. ball, et al., Journal of the Optical Society of America A, vol. 5, No. 12, pp. 2210-2219 "Age and Visual Search: Expanding the Useful Field of View", Dec. 1998.

E. Kasten, et al., Spatial Vision, vol. 10, No. 4, pp. 499-503, "Programs for Diagnosis and Therapy of Visual Field Deficits in Vision Rehabilitation", 1997.

E. Kasten, et al., Restorative Neurology and Neurology and Neuroscience, vol. 8, No. 3, pp. 113-127, "Visual Field Enlargement After Computer Training on Bran-damaged Patients Whit Homonymous Deficits: An Open Pilot Trial", Aug. 1995.

Alan Cowley, Alan Cowley, Perimetric Study of Field Defects in Monkeys After Cortical and Retinal Ablations, Quarterly Journal of Experimental Psychology, pp. 232-245, Dec. 18, 1967.

New Research on the Efficacy of NoveVision VRT Presented at 32nd Annual North American Neuro-Ophthalmology Society Meeting; Mar. 2, 2006, Business Wire © 2006.

Sharon Begley, Training the brain to see again; Sharon Begley, May 1, 2005, Saturday Evening Post, vol. 277; Issue 3; ISSN: 00489239; © Bell & Howell Information and Learning Company.

In-Sung Yoo, Advances in Medicine: New therapy gives hope to stroke victims; In-Sung Yoo, Mar. 1, 2005, The New Journal, © 2005, The New Journal.

Sharon Begley, Stroke patients have hope in sight; As part of the revolution in neurobiology, doctors are trying to train healthy brain cells to take over the visual function of neurons damaged by a stroke; Sharon Begley, Wall Street Journal, Feb. 4, 2005, The Globe and Mail.

John Dorschner, Stroke victims improve vision with computer therapy; John Dorschner, Knight Ridder Newspapers, Jul. 19, 2004, The Tallahassee Democrat, © 2004.

Sharon Begley, Survival of the Busiest—Parts of the Brain That Get Most Use Literally Expand And Rewire on Demand; Sharon Begley, Oct. 11, 2002, The Wall Street Journal, © 2002.

Patienteninformation Sehtherapie, Spectros, Nethera, http://www.teltra.org/cms/site/index.php?id=29, 2005.

Patienteninformation Sehtherapie, Otcb, Nethera, http://www.teltra.org/cms/site/index.php?id=11, 2005.

Spectros Technik/Ablauf, Nethera, Teltra, http://www.teltra.org/cms/site/index.php?id=77, 2005.

International Search Report.

* cited by examiner

F = Fixation Point
TS1 = Target Stimulus 1
VF = Visual Field
MF = Monitor Frame

*FIG. 1*

VS = Visual Field
MF = Monitor Frame
B = Blind Region
TZ = Transition Zone

TS1 = Target Stimulus 1
TS2 = Target Stimulus 2
F = Fixation Point
I = Intact Visual Field Sector

*FIG. 2*

I = Intact Visual Field Sector
FA = Fixation Anchors
MF = Monitor Frame
B = Blind Region
TS1 = Letters or Words as Target Stimuli
VF = Visual Field

SYSTEM AND METHODS FOR THE TREATMENT OF RETINAL DISEASES

CROSS REFERENCE TO RELATED APPLICATIONS

This application is a continuation-in-part of U.S. patent application Ser. No. 10/503,869, filed May 18, 2005 in the United States, which claims priority from PCT Patent Application No. PCT/EP02/01339, which was filed in English on Feb. 8, 2002, both of which are hereby incorporated by reference in their entirety.

TECHNICAL FIELD AND BACKGROUND ART

The present invention relates to the treatment of retinal diseases, and in particular, to the treatment of retinal diseases using vision restoration therapy (VRT).

Damage to the visual system, as used herein, is defined as impairment of any structure (or of all structures) involved in the processing of vision. These structures include, but are not restricted to, the nervous system tissue from the level of the retina, including the retina up to the optic nerve and all brain structures involved in process of vision. Such damage leads to visual deficits or even a loss of visual functions, which may lead to partial or more or less complete blindness. This damage may come from many sources and may include damage to the retina. Damage to the retina may be caused by various diseases including, but not limited to, retinal diseases such as glaucoma, age related macula degeneration, or retinitis pigmentosa. The retina may also be damaged by retinal detachment or laser damage. In addition, the retina may become or originate damaged based on inflammation, inherited genetic defects, metabolic issues or other causes. Damage to the retina shall be referred to herein as "retinopathies."

Retinopathies in general have not been deemed amenable to reversal using the inherent plasticity of the central nervous system (CNS), and only surgical or pharmacological interventions have been considered. That is, damage to the retina, either by disease or other means, typically requires surgery for the patient to have any restoration of vision that may have been lost.

SUMMARY OF THE INVENTION

Embodiments of the present invention may utilize a behavioral training of patients, such as a VRT, to treat damage to the retina and restore at least some (if not all) of a patient's vision. This may be accomplished by presenting visual stimuli on a simple device for emitting optical stimuli to the visual system of a human in such a way that target stimuli may be presented to various zones of the visual field: the intact sector of the visual field, to partly damages zones, or to blind regions, or all of them. Clinical tests suggest that treatment as described below may improve the vision of patients having retinal damage.

In one embodiment there is provided a method for treating a retinal disease in a human. The method of this embodiment may include locating and defining one or more zones of vision within the human's visual system and defining a treatment area which is located within at least one of the zones. The method of this embodiment may also include treating the human's retinal disease by presenting visual stimuli to the treatment area at a specified location and with a specified definition and recording changes in specified characteristics of the human's visual system. This method may also include reiterating the previous steps so as to improve the human's overall visual system.

In another embodiment there is provided a device for treating a retinal disease in a human. In this embodiment the device may include at least one optical stimuli presenting means and a fixation point means allowing the fixation of the human's view. The device of this embodiment may also include means for entering the human's response to optical stimuli perceived and means for allowing a control of the at least one optical stimuli presenting means in accordance with the performance of the human responding on optical stimuli perceived. The device of this embodiment may also include a central data processing means for recording, storing, processing and emitting data from the optical stimuli presenting means, the fixation point means, the means for entering the human's response, and the means for allowing a control of said at least one optical stimuli presenting means.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

The invention relates, generally, to a process for treating retinal diseases in a human by presenting optical stimuli to the human. The stimuli may be presented to either a zone within the intact visual field of the person or a zone outside the intact visual field of the human, or both. One of these zones is a zone to be treated, thereby allowing an improvement of the vision in general.

One feature of the present invention is that the treatment by stimulus presentation may predominantly occur in or near the zone of intact vision, but optionally also in the zone of deteriorated vision or in the zone of residual visual function or in the zone of partial visual system injury, i.e. in the transition zone. Yet another alternative would be to treat the blind region or a combination of all zones. The treatment, by presenting visual stimuli, occurs preferably only in the zone of intact vision, although a parallel or consecutive presentation of optical stimuli to at least one other zone, e.g. to the so-called "transition zone" or the blind field may occur, in addition to the presentation of stimuli to the zone of intact vision. In other embodiments, visual stimuli may only be presented to the zone outside the intact visual field.

The term "zone of intact vision" as used herein means the zone of the visual field (or brain area) which is substantially not injured or influenced by the events resulting into an impairment of the visual system, i.e. shows more or less normal visual performance when receiving optical stimuli. In contrast, the term "zone of deteriorated vision" (which is used in a similar sense as the term "zone of residual visual function" or the term "zone of partial visual system injury") is defined to mean the zone where events like accidents, stroke, degenerative diseases, or retinal diseases such as glaucoma or retinitis pigmentosa caused damages of the brain regions or the retina influencing the visual capabilities of the human so that the vision is at least partly deteriorated or even partly or completely lost. The term "blind zone" is meant to indicate those regions where a patient does not respond to stimuli at all.

Zones of intact vision, on the one hand, and zones of deteriorated or even lost vision ("blindness"), on the other hand, may be shaped continuously, i.e. as zones of a certain (e.g. round) shape, wherein the zone of said shape has more or less identical visual capabilities, as, for example intact visual capabilities. Such continuous zones may be adjacent to another (optionally similarly shaped) zone having a different visual capability as, for example, a zone of deteriorated vision, which, in turn, may be followed by a zone where the vision was completely lost. However, it may also be possible that several zones of intact vision are surrounded, in a discontinuous manner, by zones of deteriorated or lost vision. When the visual field is lost, for example, following glaucoma, a typical regional field loss (scotoma) occurs. Often, the person having experienced said event can still fixate, and the region of intact vision is in one specific area of the visual field. In the case of macula degeneration diseases or other diseases that lead to a loss of fixation ability due to loss of the function of the fovea, there may be a circular visual field that is donut-shaped, with a deficit region in the centre of the visual field (damaging the fovea) and with intact (or partially damaged) areas surrounding it (see FIG. 3).

In another embodiment the zones of intact vision are located, defined and characterized, instead of (or optionally together with) zones of impaired, i.e. deteriorated vision or residual visual function or partial visual system injury. The zones of deteriorated vision or impaired vision or partial visual system injury are hereinafter shortly referred to as "transition zones" (see FIG. 2), while the zones of intact vision are simply referred to as "zones of intact vision". Such transition zones may, for example, be found with aged people whose vision, for example peripheral vision, becomes more and more restricted. Transition zones may also be found with people whose visual system was influenced as a result of a brain injury, stroke or similar event. Another example are transition zones between zones of completely maintained and wholly lost ability to visually discriminate between colours, shapes or movements. However, in one embodiment the predominant treatment areas or treatment zones may be located in the intact vision zones.

In one embodiment, the size and location of the treatment area or areas within the intact vision zone(s) may be selected in accordance with the size, location and kind of the zone of partial visual system deterioration, of residual visual function or visual deficit of the human. In other words, it may be beneficial to check which parts of the visual system of said human offer the greatest chance for improving the overall vision by the subsequent treatment by presenting optical stimuli. In one embodiment the transition zones may be treated together with the zones of intact vision.

Based on the individual person's performance, which may be determined continuously or intermittently during the treatment, treatment stimuli may be presented in those zones of intact vision. The type, shape, intensity, duration and time sequence of the treatment stimuli is not restricted; there may be used one type of treatment stimuli or several types of treatment stimuli. In the latter case, several types may be used simultaneously or in a time sequence. In some embodiments of the invention, optical or light stimuli are presented to the person's visual system. In some embodiments the light stimuli of different colour, luminance, intensity and/or shape may be presented to the visual system of the person being treated. Such light stimuli can be presented as static light stimuli or a series of light stimuli in a sequence generating an impression of a moving object. In another embodiment, stimuli in the form of simple or more differentiated pictures of articles of daily life may be presented to the intact vision zone of the person to be treated. Such pictures may be static or moving (dynamic), according to the needs. In one embodiment of the invention optical stimuli are presented to the intact vision zone of the person to be treated, which have the form of letters, ciphers or even words or sentences. The invention, however, is not at all restricted to the above preferred embodiments of stimuli to be presented.

In a first process step, the person's visual field defect is measured. This includes the step of establishing a zone of intact visual field. The measurement is done by methods which are, as such, known from the prior art. In one embodiment of the invention, standard perimetry devices may be used, i.e. those devices, which are commonly used in the ophthalmological practice. In a preferred embodiment of the invention, a computer-based campimetric measurement is conducted. With such a device, blind, partially injured and intact sectors of the visual field can be defined.

The definition of what comprises the border between the intact zone and the partially injured zone or the intact zone and the blind zone may vary. Its position will depend on what kind of stimuli are used to define the visual function, i.e. large or small stimuli, bright or less bright stimuli, etc., the nature of the background, i.e. cluttered or simple backgrounds, and/or the timing of the stimulus, i.e. short or long presentation times.

In the second step, the zone or area of intact vision is defined, based on the measurement of the first step. The definition of the intact visual field depends on the nature of the visual stimulation selected for said definition. Stimuli which are seen more easily by the person to be treated will produce a larger apparent visual field, while stimuli which are responded to less will produce smaller apparent visual fields. Whatever method is selected to define the visual field or intact visual zone, the result of this step is a clear zone or area of vision that is defined to be intact. The shape of the intact visual field is not restricted. It may be one large area, usually round in shape, but may also consist of several intact regions which are not connected to each other.

In the third treatment step, a sequence of visual stimuli is presented to the intact visual zone of the person to be treated. The task the person to be treated has to perform is to respond, as in the prior art, to the stimulus presentation by a reaction which may be a step of pressing a key or any other input device in order to demonstrate that the stimulus—or a sequence of stimuli—was seen and recognized.

One embodiment of the present invention includes the presentation of the target stimulus to the intact vision zone(s) of the person to be treated, whereby the stimulus is selected from a library of visual objects exemplified above. The transition zone(s), near the border of blindness, may be treated in addition consecutively or may be treated in parallel. The same applies to the blind zones, which can also be selected and stimulated by presenting visual stimuli.

As the size and shape and optionally also the number of the intact vision zones may vary, the presentation of the stimuli is adjusted in such a way that the location and size of the objects fits within the boundaries of the intact vision zone(s) according to the above measurements. Of course, the "intact regions" used in this example embodiment disclosed herein could be replaced with transition zones or the blind zones. That is, the transition zones or the blind zones could be the zones being treated.

The target stimulus may be presented, for example, on a computer monitor. It could be any type of a single stimulus, or there may be selected several or many stimuli together or successively with or without different types of background. For example, useful target stimuli could be letters, words, sentences, meaningful objects (drawings, faces, photographs etc.) or objects without meaning (dots, a line pattern etc.) moving or not moving on the screen. As long as the presentation is occurring in the intact vision zone, defined as the position of the field in relation to a fixation point, and as long as the blind zone of the visual field of the person to be treated is not stimulated, any stimulus or combination of stimuli may be used.

By presenting the stimuli in the above-described way to the intact vision zone of the person to be treated, the intact vision zone is treated, and the treatment steps are repeated for treatment purposes.

In some embodiments algorithms may be used to follow the above presentation strategy, which algorithms allow the highly efficient treatment of zones or areas of visual system function (and, optionally, also dysfunction or malfunction in parallel or consecutively) and blind regions as well. The detailed steps of the treatment procedure are described below with respect to stimulating specific areas or zones of the human visual system by optical stimuli.

During the treatment step, changes in the characteristics of the visual system of the human treated are recorded. In other words: The performance of the person treated in view of visually recognizing the optical stimuli presented and himself/herself presenting the desired reaction on said visual recognition step is recorded by the system/device of the present invention. To give just one example: The reaction time of the treated person on an optical stimulus presented to the intact zone of his/her visual system is measured, and the time elapsed between the emission of the optical stimulus and the reaction given (for example by pressing a button of the device), relative to an average time value measured before for the treated person as a base line value, is taken as the performance of the person with respect to the treated area of the intact zone. However, this example is not to be considered as limiting the invention; any other appropriate step may be taken, too, in order to continuously or intermittently record changes in the characteristics of the human's visual system.

In one embodiment, the reaction of the person to be treated upon the presentation of one stimulus or several or many stimuli is measured, and the performance of the person is rewarded. This may happen in a way that reward points are added to a "reward account" when the responses fulfill a predetermined criterion. For example, when the person to be treated is instructed to perform as fast as possible, reward points are added to the reward account only in those cases where the response is recorded within a predetermined time delay (reaction time). Alternatively, reward points could be assigned to the reward account when a discrimination is properly made (e.g. correct form; correct colour; time discrimination). Based on the continuous recordal of the changes in the characteristics as described above, the location and definition of the intact zone is adapted to said changes. This may also be conducted continuously or intermittently. In a preferred embodiment of the invention, the number of reward points is used to automatically increase the difficulty of the next task. In this way, a means to increase the treatment difficulty is provided, depending upon the recordal of the reaction/response shown by the person to be treated. In other words: depending upon the performance of the treated person in processing the presented optical stimuli by the visual system, the intact visual zone is newly defined. Without wanting to be bound by the explanation, it can be assumed that, due to the effective treatment of the defined intact visual zone, the vision of the treated person is improved in said intact vision zone, specifically, and in general, for example by improving any function of the visual system (e.g. peripheral vision, visual acuity, ability to discriminate between different colours, shapes, movement; reduction of squinting; increase of the visual angle) or improving visual functions in general or removing partial visual system injuries. As a result thereof, the intact vision zone is enlarged or at least improved with respect to its contribution to the person's vision. As found in practice, the person to be treated experienced an improvement of the overall vision subjectively and due to a better performance in the treatment.

By reiterating the above-described steps, the human's intact visual field is continuously extended into zones which were previously located and defined to be transition zones.

Treatment may be carried out with a personal computer for use at home where persons to be treated practiced on a regular basis. In one embodiment daily treatment for 1 hr in a darkened room for an extended time period may be performed, as for example a 6-months period as employed in this test. However, any other treatment period may also prove efficacious.

One algorithm produces on a monitor an emission of light stimuli effecting a repetitive visual stimulation of the zone to be treated. In a first step, the zone was located, defined and characterized, i.e. there occurred a determination of the exact visual function in the zone with respect to location, size and kind.

Then there was defined a treatment area which is located within the zone. Said treatment area is a region within the zone where a regeneration of the neuronal structures of the person's visual system could be expected due to the results of the definition and characterization of the intact vision zone in the first step, e.g. due to the presence of a certain number of remaining neuronal structures.

In a subsequent step, there was conducted a stimulation of the zone based on the performance determined in the first and second steps.

Also, unlike prior art devices in which the program only stores the data for a later analysis, the present invention adapts, on a continuous or intermittent basis, treatment algorithms to the visual system performance in or near the zone being trained.

In addition, daily therapy results can be stored on suitable storing media like a tape or a disc which permits monitoring of compliance and which allows the therapy strategy to be adapted to the progress of the person.

The invention is hereinafter described in detail with reference to the Figures. While the description of the invention mainly relates to treating persons whose visual system is severely damaged, all details of the invention, i.e. the process and the apparatus, can be applied mutatis mutandis by a skilled person to the treatment of persons whose visual system deteriorates smoothly due to an ageing of said person and also to persons whose regular vision is to be treated in order to maintain the quality of the vision on a high level. Insofar, the description of the treatment procedure in connection to persons with a severely damaged visual system, and particularly a damaged retina, but having intact vision areas is not to be construed as a limitation of the invention.

Figure 1:
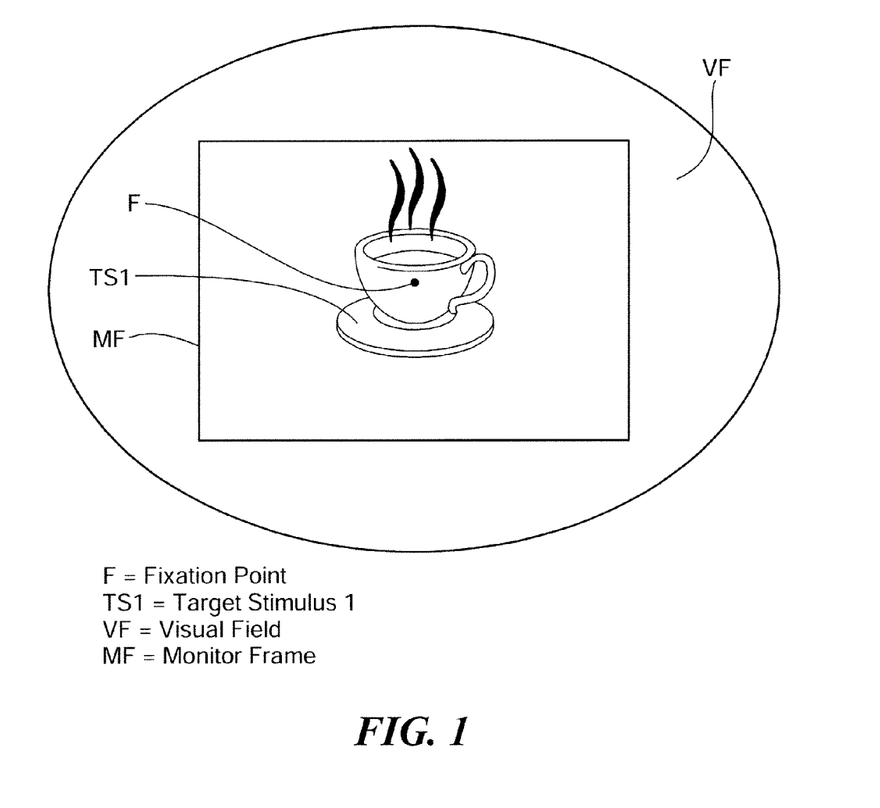
FIG. 1 represents vision in a normal visual field.

In the Figures,

FIG. 1 shows the case of visual field treatment in a normal case where the intact vision zone has been defined to have a circular shape at least covering or even overlapping the field of the monitor frame where the target stimulus is presented.

The fixation point for fixing the eyes of the person to be treated is presented in the middle of the intact vision zone, as is the target stimulus to be recognized by the person.

Figure 2:
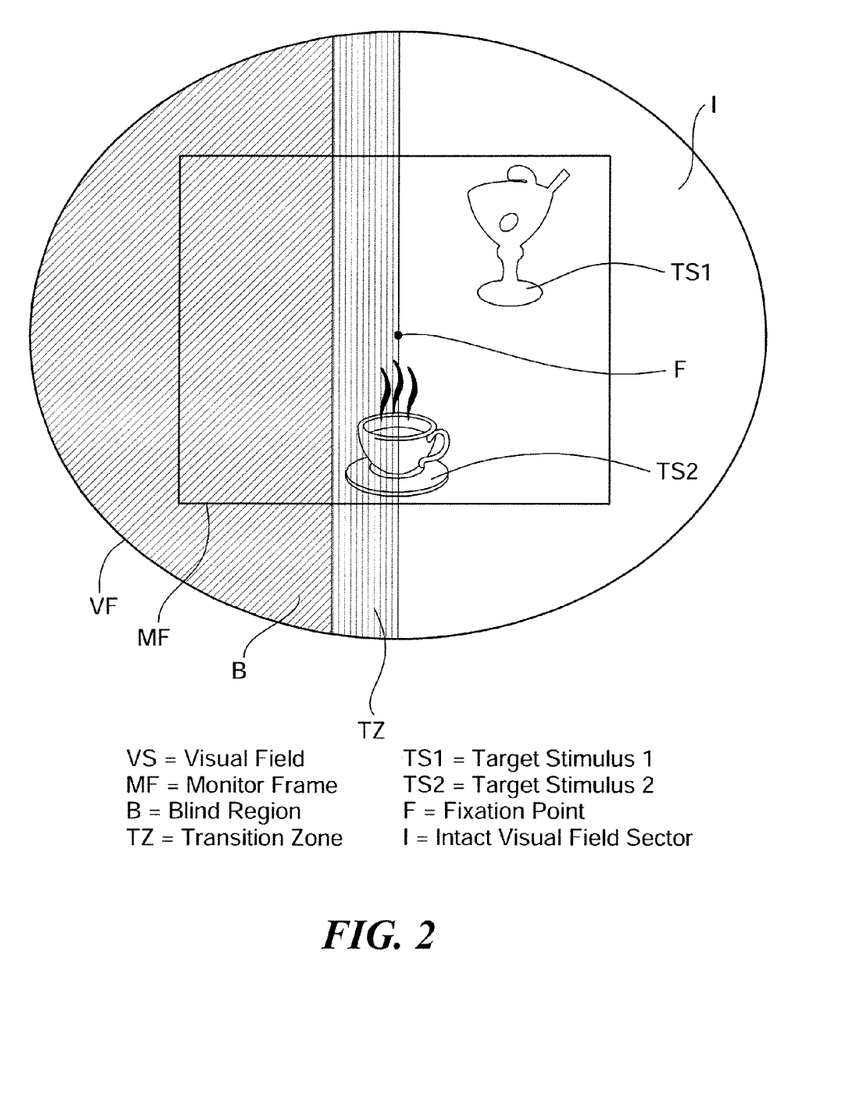
FIG. 2 represents a visual field where one hemisphere does not function.

FIG. 2 shows the case where the visual system in one hemisphere does not function; the fixation point is presented in the intact vision zone, as is the target stimulus "TS1", i.e. the stimulus treatment the intact vision field, while another target stimulus "TS2" is presented partly in the intact and partly in the injured field, independently.

Figure 3:
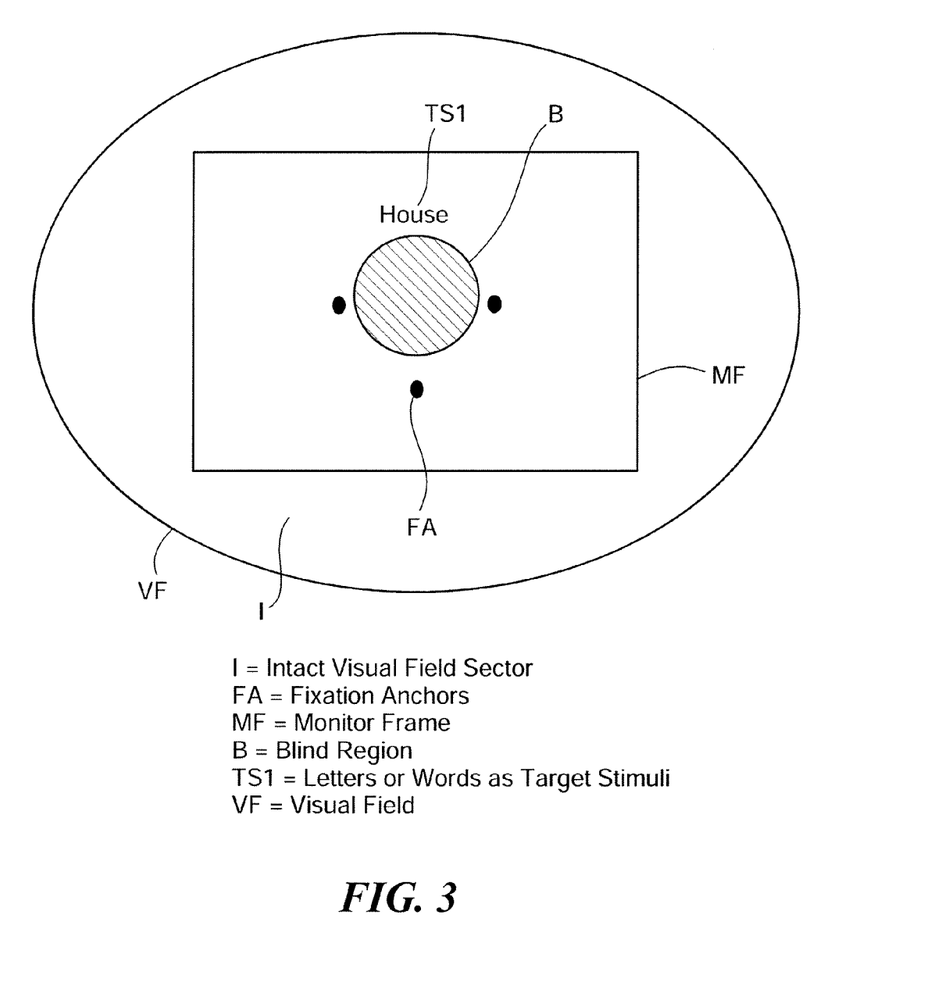
FIG. 3 represents a visual field where the central area of the visual field is injured.

FIG. 3 shows the case where the central area of the visual system (e.g., where the fovea is located) is injured ("donut-shaped visual field"). In such a case, the fixation point cannot be presented in the central area (due to the injury, it would not be recognized), but so-called "fixation anchors" are presented in the peripheral part of the blind region where the intact vision zone is located and defined. Then, a visual stimulus is presented in the intact vision zone, in this case in the form of a word.

Figure 4:
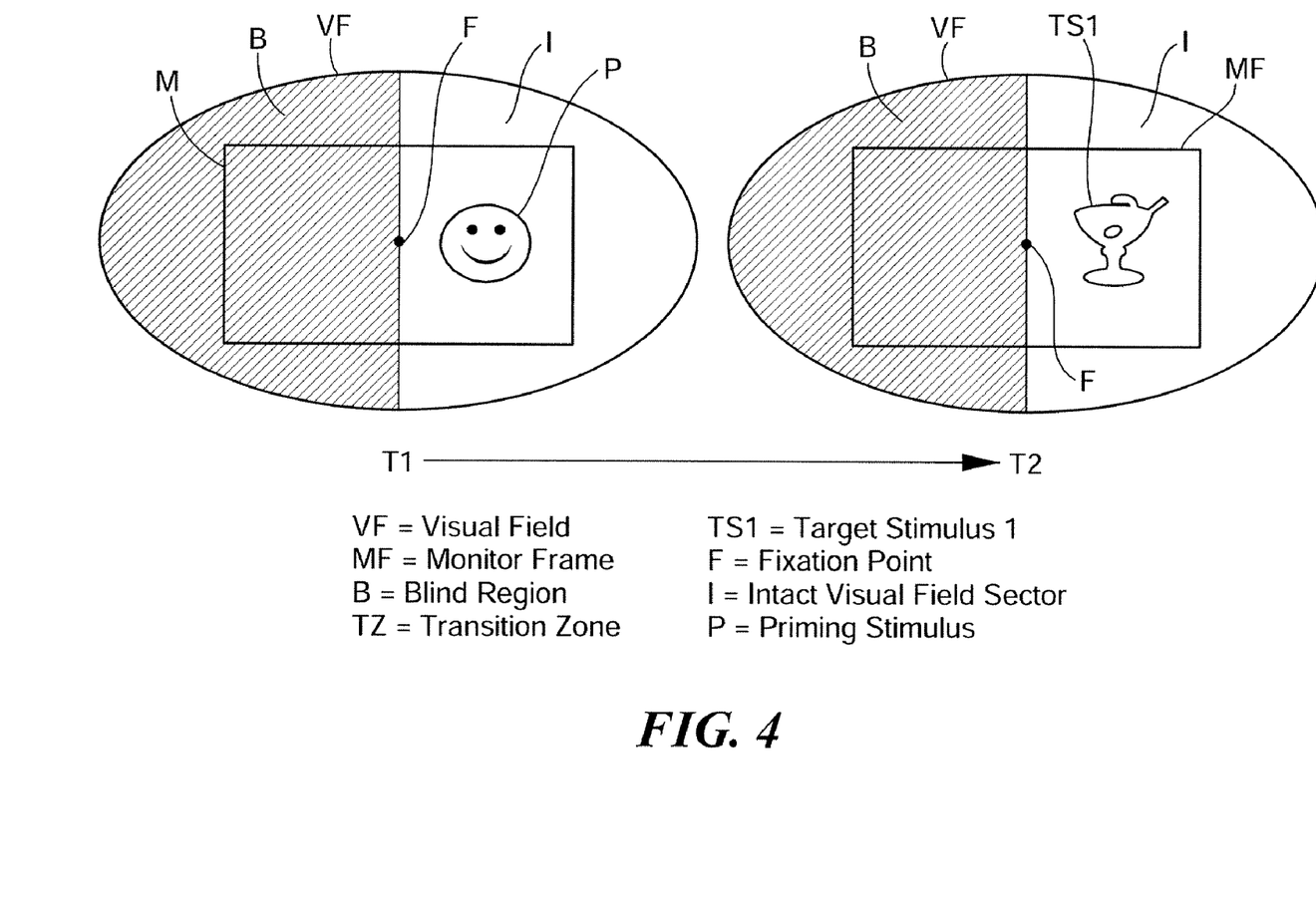
FIG. 4 shows the presentation of two stimuli in sequence.

FIG. 4 shows the case of a presentation of two stimuli in sequence (T1 and thereafter T2). In the same way as in FIG. 2, the visual field is intact in one part (I=intact visual field sector) and partially blind in another part (B=blind region). A priming stimulus (P) is preceding the target stimulus (TS1) in order to increase the probability of detecting and recognizing the target.

Figure 5:
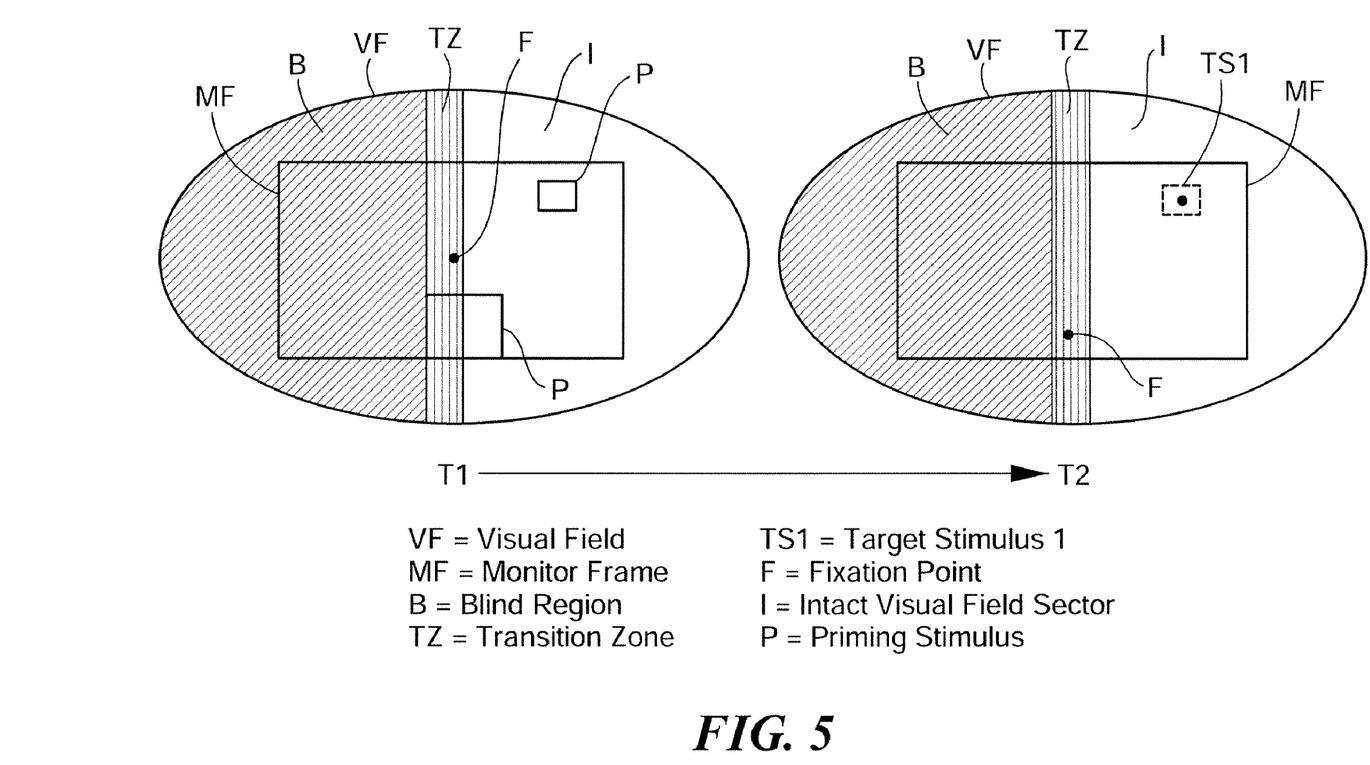
FIG. 5 shows another presentation of two stimuli in sequence.

FIG. 5 shows another case of a presentation of two stimuli in sequence (T1 and thereafter T2). In the same way as in FIG. 2, the visual field is intact in one sector (I=intact visual field sector) and partially blind in another sector (B=blind region). One of two priming stimuli P1 and P2 is presented to the person to be treated, and thereafter, one target stimulus (TS1) is presented to the intact zone of the visual field. The person will have to respond by discriminating whether a target stimulus were presented to the intact vision field in the area of the priming stimulus.

The invention is explained in further detail with reference to the Figures and the preferred embodiments of Examples 1 to 5 without being restricted to these preferred embodiments.

The computer algorithms for the step of presenting visual stimuli to the human's visual system are such that the monitor presents a fixation point, which can be presented in any part of the monitor. The fixation point serves to a fixation of the person's view to a certain point in order to allow an adjustment of the person's angle of view. In succession, additional visual stimuli are presented in or immediately adjacent to the intact vision zone, the location of which is determined in the previous step and changed in accordance with the person's performance. In the prior art device published by Kasten et al., the visual stimuli were presented independent of the persons' actual progress and were therefore inefficient and laborious. In contrast thereto, the visual stimuli are presented in the present invention predominantly in or adjacent to the intact vision zone, i.e. an area with almost no or only slight visual system injury or deteriorated vision.

EXAMPLE 1

One preferred embodiment is intended for persons to be treated having a damage of the brain's visual system. For example, when the visual system in one hemisphere does not function, the opposite sector of the visual field is lost ("hemianopsia"); see FIG. 2. In this case, the device of the present invention would present target stimuli only in the intact vision field and not in the deficient half field. Depending upon responses to the presentation of the stimuli, increasingly more difficult target stimuli are selected to which the person to be treated has to respond until no further progress in performance can be achieved.

EXAMPLE 2

Another embodiment of the invention is useful in cases where the central area of the visual system, where the fovea is located, is injured; see FIG. 3. This may occur after retinal damages such as age-related macular degeneration. The person to be treated sees little of nothing centrally, but has a donut-like visual field with no vision in the centre but intact vision in the peripheral part of the visual system. The device of the present invention generates target stimuli (in this case letters or words) in the intact vision zone near the visual field border, i.e. above or below the damaged region and positioned near the border. The letters or words may be stationary or moving, depending, e.g. upon the difficulty of the response requested.

EXAMPLE 3

In another embodiment of the present invention (exemplified in FIG. 4), a target stimulus is preceded by a priming stimulus. This could be a priming stimulus with an emotional content (e.g. a "Smiley" or "Happy Face"), which preceding priming stimulus could increase the probability of detecting the subsequent target stimulus. Both stimuli are presented to the intact vision zone of the person to be treated. In one embodiment, the priming stimulus could be presented in a very short time so that it cannot be seen consciously by the person to be treated. The person would not be asked to respond to the priming stimulus. As could be found, the presentation of a priming stimulus influences the person's ability of detection of the target stimulus.

EXAMPLE 4

Another embodiment of the invention is directed to a case where two target stimuli are presented either in rapid succession or simultaneously. The response requested from the person to be treated is a discrimination whether one or several target stimuli were presented. The person would receive award points only when the discrimination problem was responded to correctly.

EXAMPLE 5

In yet another embodiment of the invention, reward points are entered into the treatment person's reward account only for responses which fulfill a predetermined criterion. For example, reward points could be given only if a response is recorded by the computer within a predetermined reaction time or following the correct response to a discrimination task. Preferably, the target stimulus/stimuli is/are presented to the intact vision zone, although a simultaneous or consecutive presentation of one or more than one stimulus/stimuli to the intact vision zone and the transition zone may be possible and also in the frame of the present invention.

EXAMPLE 6

In another embodiment of the invention (see FIG. 5), the priming stimulus (P1, P2) may be an attention cue such as a window frame or another object which is located at the identical position as the subsequent target stimulus (TS1) presented to the intact vision zone. In this case (or also other cases), the fixation point (F in FIG. 5) may be presented to the intact vision zone or the transition zone, i.e. in a zone where the person to be treated has at least sufficient vision capability to recognize the fixation point for a fixation of his eyes or to the blind zone.

It should be apparent from this disclosure that it is beneficial treatment to those parts or the visual field which are injured or deteriorated based on damage to the retina. Of course, the actual stimulus presented can vary in size, luminance, shape or color and it can be presented by various means, such as a projection screen, a simple computer monitor or other visual projection devices such as virtual reality goggles or helmet. The type of stimulus as well as the way by which it is presented is not limited.

Although the above discussion disclosed various exemplary embodiments of the invention, it should be apparent that those skilled in the art can make various modifications that will achieve some of the advantages of the invention without departing from the true scope of the invention.

What is claimed is:

1. A method for treating a retinal disease, the method comprising:
    selecting a person having a retinal defect affecting a portion of a visual field of the person;
    locating and defining one or more zones of vision within the person's visual field;
    defining a treatment area which is located within at least one of the zones of vision;
    concurrently displaying, to the person, a plurality of fixation anchors lying within the person's visual field and surrounding the affected portion of a person's visual field;
    treating at least one zone of vision by presenting visual stimuli to the treatment area at specified locations;
    recording changes in specified characteristics of the person's visual field; and
    iterating at least the steps of defining a treatment area, presenting visual stimuli, and recording the changes so as to improve the person's overall vision.

2. The method of claim 1, wherein iterating includes adapting the locations of the presented visual stimuli according to the changes in the specified characteristics of the person's visual field.

3. The method of claim 1, wherein the person's visual field includes a zone of intact vision and the treating includes presenting visual stimuli to the zone of intact vision.

4. The method of claim 1, wherein the person's visual field includes a transition zone and
    wherein the presenting visual stimuli includes treating the transition zone.

5. The method of claim 1, wherein the person's visual field includes a blind zone and the presenting visual stimuli includes treating the blind zone.

6. The method of claim 1, wherein the treatment area has a size, a location and a kind selected in accordance with a size, a location and a kind of at least one of the zone of intact vision, the transition zone, and the blind zone.

7. The method of claim 1, wherein the visual stimuli are light stimuli of at least one of different color, luminance, intensity, and shape.

8. The method of claim 1, wherein substantially all visual stimuli are presented in or immediately adjacent to the zone of intact vision.

9. The method of claim 1, wherein the visual stimuli are presented on a screen.

10. The method of claim 9, wherein the screen is selected from the group consisting of a computer screen, a video screen, and a projection screen.

11. The method of claim 1, wherein the visual stimuli are presented on a visual projection device.

12. The method of claim 11, where in the visual projection device includes virtual reality goggles or a helmet.

13. The method of claim 1, wherein the recording changes in the specified characteristics of the person's visual field comprises recording at least one of responsiveness, color recognition, shape recognition, and localization of the visual stimuli by the person.

14. The method of claim 1, wherein at least one of the steps of locating and defining one or more zones of vision, defining a treatment area, displaying a frame, presenting visual stimuli, recording changes and iterating is controlled by a central data processing means.

15. The method of claim 1, wherein the recording changes includes recording changes in the person's ability to discriminate visual stimuli presented either in a rapid succession or simultaneously.

16. The method of claim 15, wherein recording changes in the person's ability to discriminate visual stimuli includes recording a change in at least one of the person's ability to change a reaction time after appearance of a stimulus, the person's ability to estimate time intervals between the appearance of two stimuli, and the person's ability to discriminate time-connected patterns of stimuli.

17. The method of claim 1, wherein the retinal disease is glaucoma.

18. The method of claim 1, wherein the retinal disease is retinitis pigmentosa.

19. The method of claim 1, further comprising adjusting sizes of the visual stimuli according to a size of a zone to be treated.

20. The method of claim 1 further comprising crediting a reward account according to a desired patient performance.

21. The method of claim 1, further comprising presenting a priming stimulus.

22. The method of claim 1, further comprising:
    adapting at least one of the specified locations and specified definitions of the visual stimuli according to the changes in specified characteristics of the person's visual field.

23. The method of claim 22, wherein the adapting is performed automatically.

24. The method of claim 23, wherein the adapting is based on an accumulation of points.

25. The method of claim 24, wherein the points are awarded when responses of the person to the presenting the visual stimuli fulfill a criterion.

26. The method of claim 1, wherein the retinal disease is macular degeneration.

27. The method of claim 11, where in the visual projection device includes a head-mounted display.

28. A device for treating a retinal disease affecting a portion of a person's visual field, the device comprising:
    identifying means for locating and defining one or more zones of vision within the person's visual field;
    means for concurrently displaying, to the person, a plurality of fixation anchors lying within the person's visual field and surrounding the affected portion of a person's visual field;
    means for presenting at least one optical stimulus;
    means for entering the person's response to the at least one optical stimulus;

controlling means for allowing a control of the means for presenting the at least one optical stimulus in accordance with the person's response to the presentation of the at least one optical stimulus; and central data processing means for recording, storing, processing and emitting data from the means for presenting, the means for concurrently displaying, the means for entering, and the controlling means.

29. The device of claim 28, the device further comprising:
means for defining a treatment area which is located within at least one of said zones of vision;
means for treating at least one zone of vision by presenting the at least one optical stimulus to the person's visual field;
recordation means for recording changes in specified characteristics of the person's visual system;
means for adapting a location and a definition of the at least one optical stimulus presented to said at least one zone of vision, according to said changes in specified characteristics of the person's visual system; and
means for iterating at least the presenting at least one optical stimulus, the concurrently displaying a plurality of fixation anchors, the entering the person's response, and the adapting a location and a definition continuously so as to improve the human's overall visual system,
wherein the one or more zones of vision include a zone of intact vision and a transition zone.

30. The device of claim 29, wherein only the zone of intact vision is treated.

31. The device of claim 29, wherein the zone of intact vision and the transition zone are treated.

32. The device of claim 28, additionally comprising means for at least one of fixing and supporting the head of the human.

33. The device of claim 28, wherein the means for presenting are light emitting means.

34. The device of claim 33, wherein the light emitting means are emit light characterized by at least one of variable color, luminance, intensity, and shape.

35. The device of claim 33, wherein said light emitting means includes a screen.

36. The device of claim 35, wherein the screen is selected from a group consisting of a computer screen, a video screen, or a projection screen.

37. The device of claim 33, wherein said light emitting means includes a visual projection device.

38. The device of claim 37, wherein the projection device includes virtual reality goggles or a helmet.

39. The device of claim 28, wherein at least one point is a colored mark.

40. The device of claim 39, wherein said colored mark is of variable color.

41. The device of claim 28, wherein said controlling means allows a control of the means for presenting in accordance with a quality of the person's response.

42. The device of claim 28, wherein said means for entering the person's response includes a means for recording changes in the person's ability to discriminate visual stimuli presented either in rapid succession or simultaneously.

43. The device of claim 42, wherein the means for recording changes in the person's ability to discriminate visual stimuli includes a means for recording at least one of a person's ability to change reaction time after appearance of a stimulus a person's ability to estimate time intervals between the appearance of two stimuli, and a person's ability to discriminate time-connected patterns of stimuli.

44. The device of claim 29, wherein the means for adapting is automatic.

45. The device of claim 44, wherein the means for adapting adapts the location and definition based on an accumulation of points.

46. The device of claim 45, wherein the points are awarded when responses of the person fulfill a criterion.

47. The device of claim 37, wherein the projection device includes a head-mounted display.

48. A method for treating the vision of a patient, the method comprising:
locating and defining one or more zones of vision within visual field of the patient;
defining a treatment area which is located within at least one of the zones;
concurrently displaying, to the patient, a plurality of fixation points lying within the person's visual field;
treating the patient by presenting at least one visual stimulus to the treatment area at a specified location and with a specified definition;
recording changes in specified characteristics of the patient's visual field;
automatically redefining the treatment area based on the recorded changes; and
iterating at least the concurrently displaying, treating the patient, recording the changes, and automatically redefining so as to improve the patient's overall vision, wherein the iterating includes adapting the specified location and definition.

49. The method of claim 48, wherein the redefining is triggered based on accumulation of points.

50. The method of claim 49, wherein the points are awarded when responses of the patient to a presentation of the at least one optical stimulus fulfill a criterion.

51. A device for treating a retinal disease affecting a portion of a person's visual field, the device comprising:
means for locating and defining one or more zones of vision within the person's visual field, the one or more zones of vision including a zone of intact vision and a transition zone;
means for concurrently displaying, to a person, a plurality of fixation points lying within the person's visual field;
means for presenting at least one optical stimulus;
means for entering the person's response to a presentation of the at least one optical stimulus;
controlling means for allowing a control of the means for presenting the at least one optical stimulus in accordance with a response of the person to the presentation of the at least one optical stimulus; and
central data processing means for recording, storing, processing and emitting data from the means for presenting, the means for concurrently displaying, the means for entering the response, and the controlling means.

52. A device of claim 51, the device further comprising:
means for defining a treatment area located within at least one of said zones of vision;
means for treating at least one zone of vision presenting the at least one optical stimulus to the person's visual field;
means for recording changes in characteristics of the person's visual system;
means for adapting a location and a definition of the at least one optical stimulus presented to said at least one zone of vision, according to said changes in specified characteristics of the person's visual system; and
means for iterating at least the presenting at least one optical stimulus, the concurrently displaying a plurality of fixation points, the entering the person's response, and the adapting a location and a definition continuously so as to improve the human's overall visual system.

* * * * *